United States Patent [19]
Kobayashi et al.

[11] 3,985,819
[45] Oct. 12, 1976

[54] PROCESS FOR PRODUCING ALKYLNAPHTHALENES

[75] Inventors: Katsumi Kobayashi, Minoo; Iwao Dohgane, Nishinomiya; Hiromichi Okabe, Ibaraki; Kenji Tanimoto, Minoo, all of Japan

[73] Assignee: Sumitomo Chemical Company, Limited, Osaka, Japan

[22] Filed: Oct. 8, 1974

[21] Appl. No.: 513,188

[30] Foreign Application Priority Data
Oct. 9, 1973 Japan............................ 48-113711
Oct. 9, 1973 Japan............................ 48-113712

[52] U.S. Cl............... 260/671 R; 260/668 A; 260/668 F; 260/671 C; 260/671 P; 260/672 T; 260/674 N
[51] Int. Cl.²............... C07C 3/56; C07C 15/24
[58] Field of Search........ 260/671 R, 671 C, 671 M, 260/671 P, 672 T, 674 N, 668 A, 668 F

[56] References Cited
UNITED STATES PATENTS
1,667,214   4/1928   Michel............................ 260/671
2,541,882   2/1951   Moore............................ 260/671

Primary Examiner—Delbert E. Gantz
Assistant Examiner—C. E. Spresser
Attorney, Agent, or Firm—Sughrue, Rothwell, Mion, Zinn and Macpeak

[57] ABSTRACT

A process for producing alkylnaphthalenes by alkylating naphthalene with an olefin having 2 to 4 carbon atoms, which comprises (1) introducing the olefin into a solution of crude naphthalene containing thianaphthene as an impurity in a solvent having a boiling point sufficiently different from the boiling point of the naphthalene and alkylnaphthalenes produced that the solvent is separable by distillation in the presence of (i) an aluminum chloride complex consisting of (a) aluminum chloride, (b) hydrogen chloride and (c) an alkylated benzene or naphthalene, or (ii) a solid aluminum chloride which is dissolved into the reaction solution by adding gaseous hydrogen chloride simultaneously with or prior to the introducing of the olefin, (2) aging the reaction solution, and (3) recovering the resulting alkylnaphthalenes, whereby alkylnaphthalenes, containing as monoalkylnaphthalenes a predominant amount of a β-monoalkylnaphthalene, are obtained in a high yield.

6 Claims, No Drawings

PROCESS FOR PRODUCING ALKYLNAPHTHALENES

BACKGROUND OF THE INVENTION

1. Field of the Invention

The present invention relates to a method for preparing alkylnaphthalenes, and more particularly to a method wherein naphthalene containing thianaphthene as an impurity is alkylated with a lower olefin to obtain alkylnaphthalenes containing monoalkylnaphthalenes with a predominant amount of a β-monoalkylnaphthalene in a specific solvent which dissolves the naphthalene and has a boiling point sufficiently different that the solvent is separable from naphthalene and the resulting alkylnaphthalenes by distillation, using, as a catalyst, aluminum chloride complexes or a combination of solid aluminum chloride and hydrogen chloride gas which is added to the reaction system in the amount required to dissolve the aluminum chloride.

2. Description of the Prior Art

As is well known, alkylnaphthalenes are very important intermediates, irrespective of the two isomeric α and β forms, in various industrial chemical fields, for example, in the fields of dyestuffs, medicines, agricultural chemicals, synthetic resins, lubricating oils and surface active agents, and applications are now being expanded. Among alkylnaphthalenes, as β-monoalkylnaphthalene has recently attracting special interest as a material for β-naphthol and the like.

Alkylnaphthalenes are commonly prepared by alkylation of naphthalene with olefins, and a great deal of study has so far been made on the alkylation, particularly on alkylation catalysts. Catalysts such as sulfuric acid, phosphoric acid, hydrogen fluoride, boron trifluoride and aluminum chloride are now in practical use.

These catalysts, however, are not always satisfactory. For example, hydrogen fluoride and boron trifluoride are highly corrosive to the equipment irrespective of their extremely high catalytic activity, and sulfuric acid and phosphoric acid have a low catalytic activity although they are very easy to handle. On the other hand, aluminum chloride is very advantageous as a practical catalyst. Aluminium chloride has a catalytic activity which is not as high as hydrogen fluoride and boron trifluoride but which is higher than sulfuric acid and phosphoric acid, has a relatively mild corrosiveness, and is relatively easy to handle. Furthermore, a larger proportion of β-alkylnaphthalenes in the resulting alkylnaphthalenes can be obtained using aluminum chloride catalysts than using hydrogen fluoride, boron trifluoride, sulfuric acid and phosphoric acid, which is very advantageous for an object of the present invention.

However, aluminum chloride catalysts have the disadvantages that the catalytic activity is remarkably reduced by impurities in the naphthalene starting material whereby the reaction progress becomes very difficult and a great increase in the amount of catalyst used becomes necessary. Therefore, the impurities must be removed from the naphthalene by purification which is very troublesome and uneconomical.

As is well known, naphthalene as an industrial material is produced somewhat differently from other typical aromatic compounds such as benzene, toluene and xylene. That is, with the latter compounds referred to as BTX, even those which are available as an industrial material have a quite high purity in most cases, whereas naphthalene available as such is mostly a by-product produced from a manufacturing process of the iron and steel industry, and commonly has a low purity as is indicated by the name "crude naphthalene".

The composition of crude naphthalene is not always definite, and in most cases the naphthalene content is about 95 to 97%. Impurities present in the naphthalene include thianaphthene, α-methylnaphthalene, β-methylnaphthalene, quinoline and high boiling materials referred to as tar. In particular, approximately 90% of the impurities is thianaphthene although the content varies somewhat with crude naphthalenes. Therefore, most of the impurities in the crude naphthalene can be regarded as thianaphthene, and the reduction in activity of aluminum chloride catalysts may be primarily due to the thianaphthene.

SUMMARY OF THE INVENTION

A method for improving the above-described defect of aluminum chloride catalysts, which are very effective for obtaining alkylnaphthalenes containing as a major component β-alkylnaphthalenes, particularly β-monoalkylnaphthalenes, to conduct the alkylation of the crude naphthalene containing impurities without purification, has been studied and it has been found that alkylnaphthalenes containing as the monoalkylnaphthalenes a predominant amount of a β-alkylnaphthalene can be obtained directly from crude naphthalene in a high yield.

The present invention provides a process for producing alkylnaphthalenes by alkylating naphthalene with an olefin having 2 to 4 carbon atoms, such as, for example, ethylene, propylene, butene and isobutylene, which comprises (1) introducing the olefin into a solution of crude naphthalene containing thianaphthene as an impurity in a solvent having a boiling point sufficiently different from the boiling point of the naphthalene and the produced alkylnaphthalenes that the solvent is separable by distillation in the presence of either (i) an aluminum chloride complex consisting of (a) aluminum chloride, (b) hydrogen chloride and (c) an alkylated benzene or naphthalene, or (ii) solid aluminum chloride which is dissolved in the reaction system by adding gaseous hydrogen chloride simultaneously with or prior to introduction of the olefin, (2) aging the reaction mixture, and (3) recovering the resulting alkylnaphthalenes, whereby alkylnaphthalenes containing as monoalkylnaphthalenes a predominant amount of a β-alkylnaphthalene is obtained in a high yield. The alkyl group of the resulting alkylnaphthalenes includes ethyl, iso-propyl, sec-butyl and tert-butyl groups.

DETAILED DESCRIPTION OF THE INVENTION

The process of the present invention is illustrated in greater detail below.

Suitable solvents which can be used for the alkylation of crude naphthalene with a lower olefin according to the present invention are those solvents which are capable of dissolving the naphthalene, are inert to the alkylation, and have a boiling point sufficiently different from the boiling point of the naphthalene and the resulting alkylnaphthalenes that the solvent is easily separable merely by distillation.

In alkylation, in general, including the present alkylation, many of the catalysts have the function of promoting isomerization and trans-alkylation together with alkylation. In the present invention, the present aluminum chloride catalyst systems illustrated hereinafter in detail have also the function of promoting, in addition to the alkylation of naphthalene, isomerization between α- and β-alkylnaphthalenes, and trans-alkylation of naphthalene, monoalkylnaphthalenes and polyalkylnaphthalenes. It is very essential, therefore, for reaction planning to control these catalytic functions effectively.

However, the appearance of each catalytic effect is very closely related to the reaction temperature for obtaining products of a desired composition, and therefore a temperature range must be selected so that these catalytic effects can effectively be exhibited. In other words, it is necessary to select a solvent whose boiling point is within the favorable range.

The alkylation temperatures used in the present invention are preferably about 50° to 150° C, however at the aging stage after the addition of olefin during which the isomerization and the trans-alkylation take place, a temperature range of about 80° to 120° C is particularly preferred. On the other hand, an essential condition is the use of a solvent having a boiling point sufficiently different from the boiling point of the naphthalene and resulting alkylnaphthalene that the solvent is separable from the naphthalene and resulting alkylnaphthalenes by mere distillation. Therefore, from an ease of reaction operation, a solvent whose boiling point is about 80° to 120° C at atmospheric pressure is preferred.

Specific solvents which can be used in the present invention include aliphatic saturated hydrocarbons such as, preferably, n-hexane, cyclohexane, n-heptane, iso-heptane, n-octane, iso-octane and n-nonane, with n-heptane, iso-heptane and iso-octane being particularly preferred.

The amount of the solvent used is not particularly limited, and usually 0.1 to 2 parts by weight, preferably 0.2 to 1.0 part by weight, based on 1 part by weight of the naphthalene is employed.

The two catalyst systems which are used according to the present invention are illustrated in detail below.

The aluminum chloride complexes referred to herein are those which consist of benzene or naphthalene substituted with at least one ($C_1$ to $C_4$) alkyl group, aluminum chloride and hydrogen chloride. Alkylated benzenes or naphthalenes as a component of the complex depend upon the kind of alkylation for which the complex is used. The complexes usually desirably have a low viscosity in terms of handling and the alkylated compounds are preferably toluene, xylene, ethylbenzene, ethyltoluene, iso-propylbenzene, iso-propyltoluene and sec-butylbenzene and are the same alkylated compounds as those resulting from the alkylation, for example, iso-propylnaphthalene and diiso-propylnaphthalene. Of these compounds, toluene, xylene and ethylbenzene are preferred.

The aluminum chloride complexes used in the present process can be prepared according to any well-known method, for example, as described by J.F. Norris and David Rubinstein, in *J. Am. Chem. Soc.*, 61, 1136, (1939). To illustrate a typical preparation example, hydrogen chloride gas is passed through a mixture of 5 moles of toluene and 1 mole of aluminum chloride while stirring. Room temperature (about 20° to 30° C) is sufficient for the reaction to be carried out. The gas is passed through the mixture until all the solid aluminum chloride is dissolved, and then stirring is stopped and the solution is allowed to stand. The solution separates into two layers with the upper layer being residual toluene and the lower layer being a complex of toluene-aluminum chloride-hydrogen chloride, and the separated lower layer is used as a catalyst.

Thus, by using the thus obtained liquid aluminum chloride complexes, reduction in the adverse effect of thianaphthene and improvements in the handling of the catalyst can be achieved at the same time. The handling of aluminum chloride has so far been very troublesome, because it was necessary to avoid contact of the catalyst with air, particularly to avoid moisture and water to an extreme degree in order to prevent a reduction in catalytic activity. According to the present invention, however, aluminum chloride can very advantageously be handled in a liquid form.

Another catalyst system which can be used in the present invention is a combination of aluminum chloride and hydrogen chloride gas, which will be illustrated in detail. According to the present invention, the adverse effect of the thianaphthene contained in naphthalene can be minimized very effectively by permitting hydrogen chloride gas to be present in the reaction system in which the naphthalene is alkylated in the above-described solvent using an aluminum chloride catalyst, in the amount required to dissolve the catalyst.

Hydrogen chloride gas can be passed through a naphthalene-alumimnum chloride reaction system simultaneously with or prior to the addition of the olefin gas. Hydrogen chloride gas is used in that amount which is necessary to dissolve the aluminum chloride catalyst, and normally in an equi-molar amount or more to the aluminum chloride. There is no particular upper limit to the amount of hydrogen chloride gas, however, the amount is sufficient to dissolve the solid aluminum chloride in the reaction system completely. Any excess over that amount does not adversely effect the system but is generally avoided since it is uneconomical.

The amount of catalyst used depends upon a thianaphthene content of the crude naphthalene, and the amount, as aluminum chloride, is usually about 1 to about 5 mole percent, and preferably 1.5 to 3 mole percent, based on the naphthalene.

The reaction between the naphthalene and the olefin is carried out within a range of about 50° to 150° C as described above, and more precisely, the olefin is charged at 50° to 150° C, preferably 50° to 100° C, over about a period of about 10 to 60 minutes, and an aging, after the addition of the olefin during which isomerization and trans-alkylation take place, is carried out at preferably about 80° to 120° C for about 1 to 3 hours. The molar ratio of the olefin used to the naphthalene is about 0.4:1 to 2:1, preferably 0.5:1 to 1.5:1.

After completion of the reaction, the desired alkylnaphthalene is separated from the reaction mixture by a usual treatment, for example, by pouring the mixture into water in an amount 1/5 to 2 times by weight to the weight of the reaction mixture, washing with water while stirring, allowing the aqueous solution to stand, separating the oily layer obtained and then washing the oily layer while stirring with a dilute aqueous alkali followed by removing the alkali solution to obtain the desired alkylnaphthalene.

An example of the process of the present invention is illustrated in greater detail by specific reference to the isopropylation of naphthalene.

The relationship between content of thianaphthene, a typical impurity in the naphthalene, and the amounts of aluminum chloride used is as shown in Table 1, and it can be seen therefrom that thianaphthene greatly affects the catalytic activity.

Table 1

| Run No. | Naphthalene | Thianaphthene-Content of the Naphthalene (wt%) | Amount of Aluminum Chloride Used (mole% based on naphthalene) | Conversion (%) | Yield (%) |
| --- | --- | --- | --- | --- | --- |
| 1 | Reagent (special grade) | 0.32 | 1.5 | 61 | 94 |
| 2 | Reagent (first grade) | 0.81 | 2.5 | 59 | 91 |
| 3 | Reagent (special grade) + Trianaphthene | 1.50 | 3.0 | 19 | — |
| 4 | Reagent (special grade) + Thianaphthene | 1.50 | 5.0 | 24 | — |
| 5 | Reagent (special grade) + Trianaphthene | 1.50 | 7.0 | 59 | 89 |
| 6 | Purified Naphthalene* | 1.34 | 3.0 | 21 | — |
| 7 | Purified Naphthalene | 1.34 | 5.0 | 26 | — |
| 8 | Purified Naphthalene | 1.34 | 7.0 | 62 | 92 |
| 9 | Crude Naphthalene | 1.85 | 8.0 | 24 | — |
| 10 | Crude Naphthalene | 1.85 | 10.0 | 63 | 87 |
| 11 | Crude Naphthalene | 2.31 | 10.0 | 14 | — |
| 12 | Crude Naphthalene | 2.31 | 13.0 | 57 | 84 |

Note:
*Crude naphthalene was purified by recrystallization from methanol.

Every run was carried out under the same conditions. Referring to the operation specifically, the apparatus was a 300 cc cylindrical, baffle-fitted glass reactor equipped with a stirrer, reflux-condenser, thermometer and a gas-delivery glass tube. In the reactor were placed 96 g (0.75 mole) of naphthalene and 48 g of n-heptane as a solvent and the mixture was heated in a silicon oil bath. Naphthalene was dissolved at about 70° C. Commerical aluminum chloride in a lump or granular form was added thereto in a required amount, and then propylene gas in an amount of 0.8 to 1.0 time on a molar basis to the naphthalene was introduced therein at 80° C over a period of about 1 hour through the gas-delivery tube. After the propylene introduction was over, stirring was continued at 95° to 100° C for 2 hours to complete the reaction. Thereafter, the reaction solution was poured, at room temperature (about 20° to 30° C), into water of a volume of about one-fourth the volume of the reaction solution. After thorough stirring, the solution was allowed to stand and then the separated oily layer was washed with a 10% aqueous sodium hydroxide solution in a volume of one-fourth the volume of the oil. Then the aqueous alkali layer was removed to obtain an oily alkylated product.

The conversion and yield obtained from the runs are as shown in Table 1, both of which were calculated from the following equations.

$$\text{Conversion (\%)} = \frac{\text{Moles of Naphthalene Consumed}}{\text{Moles of Naphthalene Charged}} \times 100$$

$$\text{Yield (\%)} = \frac{\text{Moles of iso-Propylnaphthalene Produced**}}{\text{Moles of Naphthalene Consumed*}} \times 100$$

*Naphthalene consumed = Naphthalene charged − Naphthalene
**Sum of mono-, di- and tri-isopropylnaphthalenes.

As is clearly shown from the results in Table 1, in the isopropylation of naphthalene using aluminum chloride as a catalyst, thianaphthene contained in naphthalene adversely affects the reaction to a great extent.

If an alkylation reaction in which the thianaphthene-content involved is low is taken as a standard case (for example, Run Nos. 1 and 2), a normal and desirable alkylation condition is such that the conversion and yield are in the ranges of 60 to 65%, and 85 to 95%, respectively. When the thianaphthene-contents exceeded a certain value, it was found that a large amount of aluminum chloride, such as about 5 times on a molar basis based on thianaphthene, was required to promote the reaction, probably due to the reduction in catalytic activity of the aluminum chloride.

Next, runs were carried out under the same conditions as described above using the present aluminum chloride complexes, and the results obtained are as shown in Table 2. Table 3 shows the results obtained using the aluminum chloride-hydrogen chloride system according to the present invention. The apparatus used for the latter case was equipped with two gas-delivery tubes, one delivery tube for the propylene gas and the other delivery tube for the hydrogen chloride gas.

Table 2

| Run No. | Naphthalene | Thianaphthene-Content of the Naphthalene (wt%) | Amount of Aluminum Chloride Complex Use* (mole % based on naphthalene) | Conversion (%) | Yield (%) |
| --- | --- | --- | --- | --- | --- |
| 1 | Reagent (special grade) + Thianaphthene | 1.50 | 1.5 | 28 | — |

Table 2-continued

| Run No. | Naphthalene | Thianaphthene-Content of the Naphthalene (wt%) | Amount of Aluminum Chloride Complex Use* (mole% based on naphthalene) | Conversion (%) | Yield (%) |
| --- | --- | --- | --- | --- | --- |
| 2 | Reagent (special grade) + Thianaphthene | 1.50 | 1.8 | 54 | 93 |
| 3 | Reagent (special grade) + Thianaphthene | 1.50 | 2.0 | 61 | 92 |
| 4 | Purified Naphthalene | 1.34 | 1.5 | 44 | 94 |
| 5 | Purified Naphthalene | 1.34 | 1.7 | 58 | 92 |
| 6 | Purified Naphthalene | 1.34 | 1.9 | 63 | 90 |
| 7 | Crude Naphthalene | 1.85 | 2.5 | 41 | 93 |
| 8 | Crude Naphthalene | 1.85 | 3.0 | 62 | 90 |
| 9 | Crude Naphthalene | 2.31 | 3.0 | 21 | — |
| 10 | Crude Naphthalene | 2.31 | 3.5 | 47 | 92 |
| 11 | Crude Naphthalene | 2.31 | 4.0 | 56 | 89 |

Note:
*The figures show the molar percentage of aluminum chloride in the complex based on the naphthalene.

Table 3

| Run No. | Naphthalene | Thianaphthene-Content of the Naphthalene (wt%) | Amount of Aluminum Chloride Used (mole% based on naphthalene) | Conversion (%) | Yield (%) |
| --- | --- | --- | --- | --- | --- |
| 1 | Reagent (special grade) + Thianaphthene | 1.50 | 1.5 | 34 | — |
| 2 | Reagent (special grade) + Thianaphthene | 1.50 | 1.8 | 57 | 92 |
| 3 | Reagent (special grade) + Thianaphthene | 1.50 | 2.0 | 63 | 90 |
| 4 | Purified Naphthalene | 1.34 | 1.5 | 40 | 96 |
| 5 | Purified Naphthalene | 1.34 | 1.7 | 54 | 94 |
| 6 | Purified Naphthalene | 1.34 | 1.9 | 61 | 91 |
| 7 | Crude Naphthalene | 1.85 | 2.5 | 45 | 93 |
| 8 | Crude Naphthalene | 1.85 | 3.0 | 64 | 92 |
| 9 | Crude Naphthalene | 2.31 | 3.0 | 38 | — |
| 10 | Crude Naphthalene | 2.31 | 3.5 | 52 | 92 |
| 11 | Crude Naphthalene | 2.31 | 4.0 | 59 | 88 |

On the comparison of the results in Table 1 and Tables 2 and 3, it can clearly be seen that the effect of the present catalyst systems on the reaction is very remarkable. For example, when aluminum chloride alone is used as a catalyst, a large amount of the catalyst is required due to thianaphthene present whereas, when the catalyst systems according to the present invention are used, a very small amount of aluminum chloride, such as about one-third that required in the former case, is sufficient to allow the reaction to proceed with the conversion and yield equal to or greater than those in the former case. Thus, when the conventional catalytic amount of aluminum chloride alone is used as a catalyst for alkylation of the naphthalene, the standard conversion and yield as mentioned above can not be achieved without purification of the naphthalene starting material to a reagent-grade.

The method and effect of the present invention have been illustrated hereinbefore, however these will become even more apparent from the following examples which are only given for the purpose of illustration and not to be interpreted as limiting the invention. Unless otherwise indicated all parts, percents, ratios and the like are by weight.

EXAMPLE 1

In a 300 cc cylindrical, baffle-fitted glass reactor equipped with a stirrer, a reflux-condenser, a thermometer and a gas-delivery glass tube were placed 131.7 g of 97.2%-purity crude naphthalene containing 2.08% of thianaphthene and 60 g of n-heptane, and the mixture was heated to 70° C while stirring. To the mixture was added 16 g of aluminum chloride complex which had previously been prepared according to the method described hereinafter, and then 42 g of propylene gas was introduced therein at 85° C over a 1 hour period through the gas-delivery tube. Thereafter, the reaction solution was immediately heated to 95° C and aged at the same temperature for 2 hours.

The reaction solution thus obtained was analyzed for unreacted naphthalene and isopropyl-naphthalene and it was found from this analysis that the conversion and yield were 64% and 89%, respectively.

The aluminum chloride complex which was used in the above alkylation was prepared as follows. In a glass reactor were placed 400 g of toluene and 100 g of aluminum chloride, and then hydrogen chloride gas was slowly passed therethrough at 30° to 40° C while stirring the mixture. When the solid aluminum chloride was dissolved, stirring and gas-introduction were stopped and the solution was allowed to stand. The solution separated into two layers, the upper layer being the remaining toluene and the lower layer being the aluminum chloride complex produced. Sixteen grams of the resulting complex contained 4.65 g of aluminum chloride (3.48% on a molar basis based on the naphthalene).

EXAMPLE 2

In a reactor were placed 25 g of monoisopropylnaphthalene and 4 g of aluminum chloide, and hydrogen chloride gas was passed therethrough until the solid aluminum chloride was completely dissolved. After allowing the mixture to stand, the upper isopropylnaphthalene layer was removed to obtain the lower complex layer.

Using the total amount of isopropylnaphthalene-aluminum chloride-hydrogen chloride complex thus obtained, alkylation was carried out under the same reaction conditions and using the same apparatus as described in Example 1. The reaction solution thus obtained was analyzed and it was found that the conversion and yield were 67% and 88%, respectively.

EXAMPLE 3

Using 100 g of a polyalkylnaphthalene containing 2 to 3 isopropyl groups, 13.3 g of aluminum chloride and hydrogen chloride gas, a polyalkylnaphthalene-aluminum chloride-hydrogen chloride complex was prepared in a manner similar to that of Example 1 or 2. Then, alkylation was carried out under the same reaction conditions and using the same apparatus as described above, using 4.6 g of the complex thus obtained, 131.4 g of 97.4%-purity crude naphthalene containing 1.91% of thianaphthene and 60 g of n-heptane. The conversion and yield obtained were 69% and 85%, respectively.

EXAMPLE 4

In the same manner as described above, butylation of naphthalene was carried out using the complex obtained from 20 g of diethylbenzene, 4 g of aluminum chloride and hydrogen chloride.

In 60 g of n-heptane was dissolved 130.7 g of 97.9%-purity crude naphthalene containing 1.6% of thianaphthene at 80° C. Fifty-six grams of 2-butene gas were passed therethrough over a 1 hour period, and then the solution was kept at 100°C for 1 hour followed by after-treatment. Thus, a reaction solution containing sec-butylnaphthalene was obtained.

It was found by analysis that the conversion and yield obtained were 71% and 92%, respectively.

EXAMPLE 5

In the same apparatus as described in Example 1 were placed 131.7 g of crude naphthalene containing 2.08% of thianaphthene and 60 g of n-heptane, and then the mixture was heated to 70° C.

To the solution was added 4.91 g of a reagent-grade aluminum chloride (95% purity), and then hydrogen chloride gas and propylene gas were slowly introduced therein through separate gas-delivery tubes.

The introduction of hydrogen chloride gas was stopped when the solid aluminum chloride was completely dissolved. Forty-two grams of propylene gas were passed therethrough at 85° C over a 1 hour period. Immediately after the introduction was over, the solution was heated to 95° C and aged for 2 hours.

The reaction solution thus obtained was analyzed for unreacted naphthalene and isopropylnaphthalene produced and it was found that the conversion and yield were 62% and 93%, respectively.

REFERENCE EXAMPLE

In the same apparatus as described in Example 1 were placed the same quantity and quality of crude naphthalene and solvent as described in Example 1, and the mixture was heated to 70° C. To the mixture was added 13.3 g of aluminum chloride, and then propylene gas was introduced therein. The absorption of gas became very faint after 20 minutes and then completely ceased after 30 minutes, and thereafter all of the gas introduced passed out of the system. The reaction solution was aftertreated in a similar manner and it was found by analysis that the conversion and yield obtained were 27% and 78%, respectively.

While the invention has been described in detail and with reference to specific embodiments thereof, it will be apparent to one skilled in the art that various changes and modifications can be made therein without departing from the spirit and scope thereof.

What is claimed is:

1. A process for producing alkylnaphthalenes by alkylating naphthalene with an olefin having 2 to 4 carbon atoms, which comprises (1) introducing said olefin at a temperature of about 50° to 150° C for about 10 to 60 minutes into a solution of crude naphthalene containing thianaphthene as an impurity in an amount up to about 4.5% in a solvent selected from the group consisting of n-hexane, cyclohexane, n-heptane, iso-heptane, n-octane, iso-octane and n-nonane and having a boiling point sufficiently different from the boiling point of naphthalene and alkylnaphthalenes produced that the solvent is separable by distillation in the presence of (i) an aluminum chloride complex consisting of (a) aluminum chloride, (b) hydrogen chloride and (c) an alkylated benzene or naphthalene, or (ii) a solid aluminum chloride which is dissolved into the reaction solution by adding gaseous hydrogen chloride simultaneously with or prior to the introducing of said olefin, (2) aging the reaction solution at a temperature of about 80° to 120° C for about 1 to 3 hours, and (3) recovering the resulting alkylnaphthalenes, whereby alkylnaphthalenes containing as monoalkylnaphthalenes, a predominant amount of a β-monoalkylnaphthalene as compared to total monoalkyl-naphthalene produced, are obtained, the amount of hydrogen chloride being used in said catalyst being at least an equimolar amount per the amount of aluminum chloride used, the amount of the aluminum chloride complex (i) or the amount of the solid aluminum chloride (ii) converted to an aluminum chloride basis is about 1.0 to about 5.0% on a molar basis on the naphthalene feed.

2. The process according to claim 1, wherein the olefin is used in an amount of 0.4 to 2 times on a molar basis based on the naphthalene.

3. The process according to claim 1, wherein the aluminum chloride catalyst (i) consists essentially of (a) aluminum chloride, (b) hydrogen chloride and (c) toluene, xylene, ethylbenzene, ethyltoluene, isopropylbenzene, isopropylbenzene, iso-propyltoluene, sec-butylbenzene, isopropylnaphthalene or diisopropylnaphthalene.

4. The process according to claim 1, wherein the olefin is ethylene, propylene, butene or isobutylene.

5. The process according to claim 1, wherein the alkyl group of the resulting alkylnaphthalenes is an ethyl group, an iso-propyl group, a sec-butyl group or a tert-butyl group.

6. In a process for producing an alkylnaphthalene by alkylating naphthalene with an olefin having 2 to 4 carbon atoms in the presence of a catalyst, the improvement which comprises alkylating crude naphthalene containing thianaphthene as an impurity in an amount up to about 4.5% using a solvent selected from the group consisting of n-hexane, cyclohexane, n-heptane, iso-heptane, n-octane, iso-octane and n-nonane which is capable of dissolving said crude naphthalene and which has a boiling point sufficiently different from the boiling point of the naphthalene and the alkylnaphthalenes produced that the solvent is separable by distillation, said olefin being introduced into said solvent at a temperature of about 50° C to 150° C for about 10 to 60 minutes and using as the catalyst (i) an aluminum chloride complex consisting essentially of (a) aluminum chloride, (b) hydrogen chloride and (c) an alkylated benzene or naphthalene, or (ii) a solid aluminum chloride which is dissolved in the reaction solution by adding gaseous hydrogen chloride simultaneously with or prior to the introducing of said olefin, and ageing the reaction solution at a temperature of about 80° to 120° C for about 1 to 3 hours whereby alkylnaphthalenes containing as monoalkylnaphthalenes a predominant amount of a β-monoalkylnaphthalene as compared to total monoalkylnaphthalene produced, are obtained, the amount of hydrogen chloride being used in said catalyst being at least an equipmolar amount per the amount of aluminum chloride used and the amount of the aluminum chloride complex (i) or the amount of the solid aluminum chloride (ii) converted to an aluminum chloride basis is about 1.0 to about 5.0% on a molar basis based on the naphthalene feed.

* * * * *